(12) United States Patent
Pang et al.

(10) Patent No.: US 11,452,684 B2
(45) Date of Patent: Sep. 27, 2022

(54) MASCARA COMPOSITIONS AND METHODS

(71) Applicant: L'OREAL, Paris (FR)

(72) Inventors: Christopher Pang, New York, NY (US); Jody Ebanks, Bloomfield, NJ (US); Hy Si Bui, Piscataway, NJ (US); Xian Zhi Zhou, Millburn, NJ (US)

(73) Assignee: L'OREAL, Paris (FR)

( * ) Notice: Subject to any disclaimer, the term of this patent is extended or adjusted under 35 U.S.C. 154(b) by 542 days.

(21) Appl. No.: 16/369,489

(22) Filed: Mar. 29, 2019

(65) Prior Publication Data
US 2020/0306169 A1    Oct. 1, 2020

(51) Int. Cl.
A61K 8/92     (2006.01)
A61Q 1/10     (2006.01)
A61K 8/72     (2006.01)
A61K 8/81     (2006.01)

(52) U.S. Cl.
CPC ............... A61K 8/92 (2013.01); A61K 8/72 (2013.01); A61K 8/8182 (2013.01); A61Q 1/10 (2013.01); A61K 2800/884 (2013.01)

(58) Field of Classification Search
None
See application file for complete search history.

(56) References Cited

U.S. PATENT DOCUMENTS

| 6,214,326 | B1 | 4/2001 | Dupuis |
| 6,517,823 | B1 | 2/2003 | Norman et al. |
| 7,504,093 | B2 | 3/2009 | Bracken et al. |
| 2012/0327465 | A1 | 12/2012 | Yamada |
| 2013/0164241 | A1* | 6/2013 | Foley ............... A61K 8/8141 424/70.7 |
| 2016/0175219 | A1 | 6/2016 | Washington et al. |
| 2017/0035679 | A1 | 2/2017 | Douezan et al. |
| 2017/0065512 | A1 | 3/2017 | Zhu et al. |

FOREIGN PATENT DOCUMENTS

| WO | 2010014328 A2 | 2/2010 |
| WO | 2017044546 A1 | 3/2017 |

OTHER PUBLICATIONS

BASF "Luviset Clear AT 3" <https://carecreations.basf.us/products/luviset-clear-at-3> accessed Oct. 2021 (Year: 2018).*
"Waterproof Eyebrow Mascara," MINTEL GNPD, record ID 3650969, published Dec. 2015, p. 1-3.

* cited by examiner

Primary Examiner — Nicole P Babson
(74) Attorney, Agent, or Firm — Oblon, McClelland, Maier & Neustadt, L.L.P.

(57) ABSTRACT

A kit includes primer composition includes a vehicle comprising water and one or more first film-forming polymers stabilized in the vehicle, wherein the first film-forming polymer that is a non-ionic and water-soluble or water dispersible copolymer comprising a cyclic amide monomer, a cyclic amine monomer, and an acrylamide monomer. It further includes a mascara composition including water; colorant; wax; emulsifier; and one or more second polymers. The mascara composition has a critical shear rate from 2.5/s to 100/s. Methods of applying makeup to the eyelashes are also provided.

18 Claims, 1 Drawing Sheet

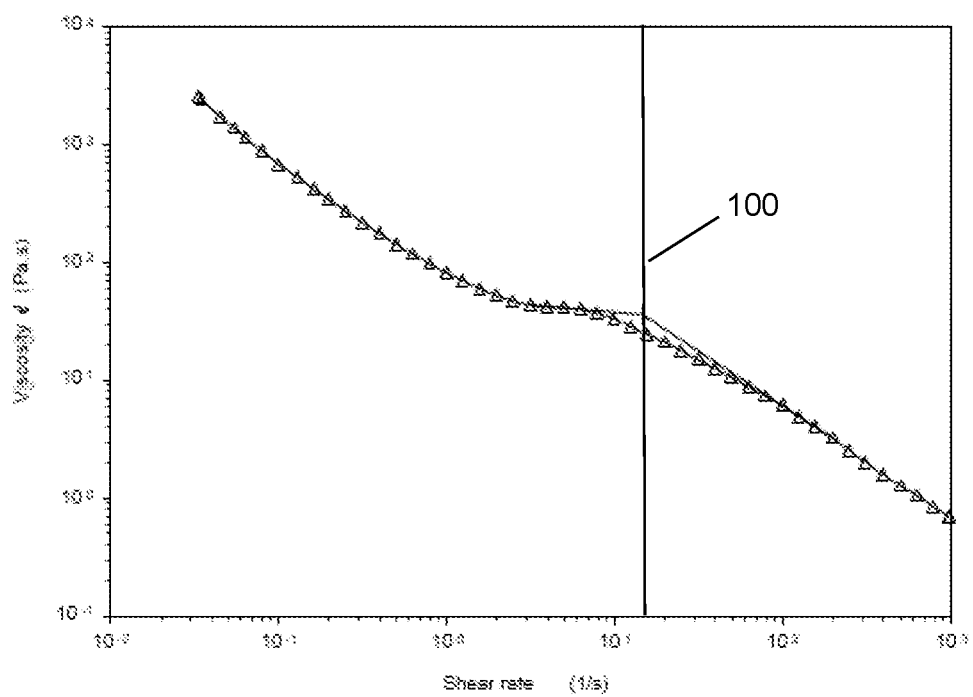

MASCARA COMPOSITIONS AND METHODS

FIELD OF THE INVENTION

The present invention relates to cosmetic compositions for keratinous materials such as keratin fibers. The cosmetic compositions are preferably applied to eyelashes.

DISCUSSION OF THE BACKGROUND

Mascara compositions are commonly used to enhance the appearance of eyelashes. Conventional mascara compositions generally use waxes to form crystalline network structures to enhance curl, volume, length, thickness, and/or colors to eyelashes. However, mascara many compositions become less resistant to oil and/or sebum, causing smearing, flaking, and/or color transferring after wearing for a certain amount of time. Furthermore, while conventional mascara can be used to assist in moderate curl formation eyelashes, users of mascara typically are forced to rely on particular applicators or eye-lash curling devices to enhance curl to any substantial degree.

The inventors of the present invention have found that certain mascara formulations are actually useful for inducing a curling effect and lastingness to eyelashes as compared to conventional mascara formulations when used in conjunction with particular 'primer' compositions.

Accordingly, one aspect of the present invention is a kit including two separate compositions which together are able to impart an enhanced appearance to the eyelashes by enhancing eyelash curling. Another aspect of the present invention is directed to a method of making up eyelashes to enhance physical appearance of the eyelashes.

BRIEF DESCRIPTION OF DRAWINGS

The FIGURE depicts the results of a plot of viscosity versus shear rate and the identification of a critical shear rate consistent with embodiments of the invention described herein.

SUMMARY OF THE INVENTION

According to certain embodiments of the present invention, a kit is provided. The kit includes primer composition. The primer composition includes water and a non-ionic and water-soluble or water dispersible copolymer including a cyclic amide monomer, a cyclic amine monomer, and an acrylamide monomer. The kit further includes a mascara composition that includes water, colorant, wax, emulsifier; and one or more second polymers. The mascara composition has a critical shear rate from 2.5/s to 100/s.

According to certain embodiments of the present invention, methods of applying makeup to the eyelashes are provided. The method includes applying a primer composition to the eyelashes. The primer composition includes water and a non-ionic and water-soluble or water dispersible copolymer comprising a cyclic amide monomer, a cyclic amine monomer, and an acrylamide monomer. The method further includes applying to the eyelashes having the primer composition previously applied thereto, a mascara composition. The mascara composition includes water, pigment, wax, emulsifier and one or more second polymers. The mascara composition has a critical shear rate from 2.5/s to 100/s.

It is to be understood that both the foregoing general description and the following detailed description are exemplary and explanatory only, and are not restrictive of the invention.

DETAILED DESCRIPTION OF THE INVENTION

Unless otherwise indicated, all numbers expressing quantities of ingredients and/or reaction conditions are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, the expression "at least one" means one or more and thus includes individual components as well as mixtures/combinations.

As used herein, "kit," means a plurality of separate compositions, each of which are co-packaged together. Individual compositions within a kit may be meant to be used in conjunction with one another.

As used herein, "primer composition," "mascara," "mascara composition" mean compositions that are intended to be applied to keratinous materials, preferably keratin fibers, in particular eyelashes and/or eyebrows, further in particular eyelashes.

As used herein, "keratinous materials" include, but are not limited to, skin, nail, living keratin fibers such as head hair, eyelashes, and eyebrows, and non-living keratin fibers such as swatches, extensions, and false eyelashes. The living and non-living keratin fibers include any mammalian hair, including human hair.

"Percent" or "%" as used herein, when referring to concentrations of ingredients or components in compositions refers to percent by weight. Unless otherwise specifically stated, the percent of a particular ingredient or ingredients is on an actives basis and is relative to the entire mascara composition.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

Other than in the operating examples, or where otherwise indicated, all numbers expressing quantities of ingredients and/or reaction conditions are to be understood as being modified in all instances by the term "about," meaning within 10% to 15% of the indicated number, such as within about 5% of the indicated number.

"Solids basis" or "actives basis" refers to the amount of a particular ingredient exclusive of any solvents, carriers, impurities and the like that may be supplied with the particular ingredient "Substantially free" as used herein to refer to the presence of ingredients within compositions of the present invention, means that the particular ingredient is present in concentrations by weight of less than about 1%, such as less than about 0.5%, such as less than about 0.25%, such as about 0%.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "self-curling" refers to an attribute associated with compositions of the present invention. Self-curling refers to the ability of a composition to induce curling on eyelashes upon drying—and not from use of an applicator that is specifically to induce curling. Self-curling may be measured using the SELF-CURLING TEST noted in this specification.

Primer Composition

According to the present invention, the inventors have found that particular primer compositions comprising a film-forming polymer portion have surprising and unexpected properties such as those related to self-curling. These compositions include a one or more film-forming polymers that include a non-ionic water-soluble or water dispersible copolymer comprising a cyclic amide monomer, a cyclic amine monomer, and an acrylamide monomer.

Film-Forming Polymer Portion

Primer compositions of the present invention include one or more film-forming polymers ("first film-forming polymers") that include a non-ionic water-soluble or water dispersible copolymer comprising a cyclic amide monomer, a cyclic amine monomer, and an acrylamide monomer. The one or more film-forming polymers may be part of a film-forming polymer portion. One of ordinary skill in the art will readily appreciate the term "film-forming polymer" refers or "film forming agent" as used herein means a polymer or resin that leaves a film (e.g., a continuous film) on the substrate to which it is applied, for example, after a solvent accompanying the film former has evaporated, absorbed into and/or dissipated on or from the substrate. In order to evaluate whether a polymer is a film forming polymer a drawdown test may be performed by putting 5 to 10 grams of material on the center of a Leneta card stock (Black and White Opacity card Chart 2812 available from BYK Additives and Instruments of Geretsried, Germany) and using a 3 mil Drawdown Birdbar (also from Byk), spreading the material for across the sheet (8 in by 3 in) and allowing it to dry overnight. If the material forms a conformal coating and/or can picked up or scraped off with a razorblade to be removed as a free standing film, then it is film forming. Regardless, if it does not coat the card, cannot in any reasonable way be removed as a free-standing film and/or forms a loose powdery coating that rubs off readily onto one's finger, then it is not a film former. Film-forming polymers that are cosmetically or dermatologically acceptable may be utilized in the present invention. As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

The film forming polymer portion includes the film-forming polymer that is a non-ionic and water-soluble or water-dispersible copolymer comprising a cyclic amide monomer, a cyclic amine monomer, and an acrylamide monomer. Accordingly, the film-forming polymer that is a non-ionic and water-soluble or water-dispersible copolymer comprising a cyclic amide monomer, a cyclic amine monomer, and an acrylamide monomer will have cyclic amide, cyclic amine and acrylamide functionality. For clarity, by "non-ionic and water-soluble or water-dispersible" it is meant that the copolymer is non-ionic. The copolymer is also (either) water-soluble or water-dispersible, particularly to the extent that it can be readily stabilized throughout a vehicle (e.g., water) present in the composition.

Cyclic amide and cyclic amine monomers useful in film-forming polymers of the present invention include those having one or more aromatic or aliphatic ring structures. These rings may have sizes ranging from about having sizes of, for example, 5 to 8 ring members.

In certain embodiments of the invention, monomers useful in forming the film-forming polymers present in compositions of the present invention are polymerizable ethylenically unsaturated monomers having a cyclic amine residue or a cyclic amide residue. Accordingly, the cyclic amide monomers of the film-forming polymers useful in the present invention may include cyclic amide residues that are or include heterocyclic ring structures such as lactams and the like. These may include α-Lactam, β-lactam, γ-lactam, δ-lactam, and ε-lactam. In one notable embodiment, the cyclic amide is a pyrrolidone (a γ-lactam). Useful cyclic amine residues may include any of various heterocyclic amines such as azoles, pyrroles, pyrrolidines, carbamates, and the like. In one notable embodiment, the cyclic amine residue is an imidazole.

In certain other embodiments, acrylamide monomers useful according to the present invention include those having —$C_3H_5NO$ functional groups. Examples include (meth) acrylamides.

In certain embodiments, the non-ionic, water-soluble or water-dispersible copolymer comprising a cyclic amide monomer, a cyclic amine monomer, and an acrylamide monomer has a weight average molecular weight in a range from about 10,000 daltons to about 1,000,000 daltons.

In certain embodiments, the non-ionic, water-soluble or water-dispersible copolymer comprising a cyclic amide monomer, a cyclic amine monomer, and an acrylamide monomer is a copolymer of N-vinyl pyrrolidone, methacrylamide, and N-vinylimidazole.

In certain embodiments, the non-ionic, water-soluble or water-dispersible copolymer comprising a cyclic amide monomer, a cyclic amine monomer, and an acrylamide monomer may be a commercially available variety, such as LUVISET CLEAR AT3, commercially available from BASF of Ludwigshafen, Germany.

The concentration of the non-ionic, water-soluble or water-dispersible copolymer comprising a cyclic amide monomer, a cyclic amine monomer, and an acrylamide monomer in the mascara may notably be greater than about 7%. In certain embodiments the concentration is greater than about 10%, such as greater than about 15%. In certain other embodiments, compositions of the present invention include the non-ionic, water-soluble or water-dispersible copolymer comprising a cyclic amide monomer, a cyclic amine monomer, and an acrylamide monomer in a concentration from about 5%, 10% 15% or 20% to about 20%, 30%, 40% 50% or 60% including all combinations of such ranges.

According to certain embodiments of the invention, the film-forming polymer portion includes a primary film-forming polymer. By "primary film-forming polymer," it is meant the film forming polymer or class thereof that comprises 50% or more of the entire film forming polymer portion. According to certain notable embodiments, the non-ionic, water-soluble or water-dispersible copolymer comprising a cyclic amide monomer, a cyclic amine monomer, and an acrylamide monomer is the primary film forming polymer.

According to certain embodiments the non-ionic, water-soluble or water-dispersible copolymer including a cyclic amide monomer, a cyclic amine monomer, and an acrylamide monomer comprises 55% percent or more by weight of the film-forming polymer portion, such as about 70% or more, such as about 90% of the film-forming polymer portion.

The film-forming polymer portion may also include one or more secondary film-forming polymers. By "secondary" film-forming polymers it is meant that the combined concentration of these one or more secondary film-forming polymers in the mascara composition is less than the concentration of the primary film-forming polymer. The one or more secondary film forming polymers may be any of those that are commonly used in mascara compositions such as non-crosslinked acrylate and acrylic co-polymers, urethane polymers, polyesters. A non-limiting example of a suitable non-crosslinked secondary film-forming polymer is sodium alginate, available as PROTANAL PH 6160 from FMC Health and Nutrition of Philadelphia, Pa. The amount of secondary film-forming polymer (e.g., sodium alginate) present in the mascara composition may be any suitable amount such as in a range from about 0.25% to about 2% by weight.

In certain embodiments of the invention, the secondary film-forming polymer may include additional film-forming polymers that may be stabilized in the vehicle. Suitable additional film-forming polymers include any of various acrylate and acrylic co-polymers, urethane polymers, polyesters and the like that are commonly used in mascara compositions.

Wax

Primer compositions of the present invention may include wax. As used herein, "wax" is intended to mean a lipophilic fatty compound that is solid at room temperature (about 25° C.) and atmospheric pressure (760 mmHg, i.e., 105 Pa), which undergoes a reversible solid/liquid change of state and which has a melting point of greater than 30° C., and in some embodiments, greater than about 55° C. up to about 120° C. or even as high as about 200° C.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

In certain embodiments, compositions of the present invention include wax, such as from about 0.5%, 2% or 4% to about 5%, 10% or 20% including all combinations of such ranges. However, in certain notable embodiments, primer compositions of the present invention are substantially free of wax.

Oil

Primer compositions of the present invention may include oils. However, in certain notable embodiments, compositions of the present invention are substantially free of oils. In certain particular embodiments, compositions of the present invention have less than 0.25% of waxes and less than 0.25% of oils.

As used herein, by "oils," it is meant compounds having a melting point of less than about 30 C and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

In certain embodiments, compositions of the present invention include oils, such as from about 0.5%, 2% or 4% to about 5%, 10% or 20% including all combinations of such ranges. However, in certain notable embodiments, primer compositions of the present invention are substantially free of oils.

Surfactants and Dispersants

The film-forming polymer portion of the primer composition may provide sufficient thickening of the vehicle to obviate the need for dispersants or suspending agents. However, according to certain embodiments of the present invention, the mascara composition may further optionally include a surfactant or dispersant, primarily to assist in wetting or dispersing of the particulate portion. Any surfactants, including anionic, nonionic, amphoteric, and cationic, surfactants, may be used in the present invention, as long as the surfactant is cosmetically or dermatologically acceptable. The surfactant may be used either singly or in combination two or more thereof. In one embodiment, the mascara composition may include an anionic surfactant/dispersant such as sodium laureth sulfate.

If present, the amount of the surfactant or dispersant in the primer composition may be from about 0.1 to about 5% by weight. In certain other embodiments the concentration of dispersants and surfactants is limited to less than 1%, such as less than about 0.5%, such as less than about 0.1%.

Colorants and Particulates

Primer compositions of the present invention may optionally include at least one colorant. Suitable colorants include, but are not limited to inorganic particulates and organic pigments that impart color (including black). In particular embodiments, the colorant is selected from carbon black and iron oxides.

Other particulate materials are generally finely divided particulates that are insoluble in but are otherwise homogeneously stabilized (suspended or dispersed) in a vehicle of the composition. The one or more particulate materials are typically materials that are incapable of chemically "self-fusing" in-use and are not themselves film-forming.

Other suitable particulates are fillers that may provide opacity and include inorganic particulate materials include any of a variety of porous, semi-porous, non-porous, or hollow, coated or uncoated water-insoluble inorganic particulates such as silica, alumina, carbon and any of various oxides, silicates, aluminosilicates, nitrides, carbides, carbonates, fluorophlogopites, and the like. Other particulates, e.g., organic pigments such as lake pigments; other organic particulates such as polymeric particulates including nylon particulates, acrylate particulates (e.g., PMMA), silicone elastomer particulates, and the like may also be used.

Any of various lipophilic or water soluble dyes may be used as well. When the composition does not contain colorants, the primer composition may be a clear or transparent composition.

Vehicle

In order to facilitate application to the eyelashes, primer compositions of the present invention may include a vehicle in which the film-forming polymer portion is stabilized (i.e., dissolved, dispersed or suspended). The vehicle generally includes, consists of or consists essentially of water. In certain embodiments of the invention, the mascara compositions of the present invention include at least about 30% water, such as from about 40% to about 90%, such as from about 45% to about 85%.

Additional Ingredients

The primer composition of the present invention may further include various additives desirably used in cosmetic or dermatological compositions. For example, water, thickeners, dispersants, anti-oxidants, pH adjusters, preservatives, neutralizing agents, fragrances, fillers, co-solvents, plasticizers, cosmetic and dermatological active agents such as emollients, moisturizers, vitamins, UV filters, and sunscreens, and mixtures thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

According to certain embodiments, primer compositions of the present invention are substantially free of polyhydric alcohols such as glycerin or glycols such as propylene, butylene or hexylene glycol.

According to certain embodiments, the primer composition of the present invention is in the form of a water solution or dispersion where the non-ionic water-soluble or water dispersible copolymer comprising a cyclic amide monomer, a cyclic amine monomer, and an acrylamide monomer and one or more other ingredients are present as dissolved or dispersed in a vehicle that includes water.

According to certain embodiments the primer compositions of the present invention may have a viscosity from about 0.01 kPas, 0.1 kPas or 0.3 kPas to about 0.6 kPas, 10 kPas or 50 kPas including all combinations of such ranges, when measured at a shear rate of 1 s$^{-1}$ as measured using, for example, the AR-G2 magnetic bearing rheometer, available from TA Instruments of New Castle, Del. In order to adjust the viscosity of the mascara formulation, one may use one or more viscosity modifiers. According to certain other embodiments of the invention, the mascara may have a pH that is from about 5 to about 8.

The primer compositions of the present invention are intended to be applied onto keratinous materials such as keratin fibers, in particular, eyelashes or eyebrows. In certain notable embodiments the primer composition is applied to a portion of keratinous surface that one desires to adopt a concave curvature. In particular, the inventors have found that compositions of the present invention are useful for self-curling. When used in this regard, the primer composition is applied to the top surface of the upper eyelash and allowed to dry. By applying only to the top surface of the lashes, the lash will curl upwards upon drying.

As described above, according to one aspect of the present invention, the primer composition when used with certain mascara composition has improved cosmetic properties such as, for example, increased volume properties, increased self-curling properties, increased self-curl retention properties, increased length properties, and the like.

Mascara Compositions

The inventors have found that certain mascara compositions are surprisingly useful when used in conjunction with the above-described primer composition. In particular, according to embodiments of the invention, the mascara compositions according to embodiments of the invention include water, colorant, wax, emulsifier, and one or more polymers (also referred to herein as "second polymers"). The inventors have also further surprisingly found that such mascara composition having a critical shear rate from 2.5/s to 100/s (such as from 2.5/s to 75/s, such as 2.5/s to 50/s) provide particularly beneficial curling. In certain other embodiments, the mascara composition has a complex modulus measured at 1% strain ($G^*_{1\%}$) less than about 8500 Pa, such as less than about 8000 Pa. In certain other embodiments, the mascara composition has a viscosity measured at a shear rate of 0.1 1/s, ($\eta_{0.1}$) less than about 1500 Pa·S, such as less than about 1000 Pa·S. Complex modulus measured at 1% strain and viscosity measured at 0.1 1/s are described in more detail in the Examples below.

In a preferred embodiment, the mascara composition has a water external phase and a fatty internal phase and may be in the form of an oil-in-water emulsion. The concentration of water may range from about 25% to 65% by weight of water, such as 35% to 60%, such as about 40%-55% water.

Suitable colorants for use in the mascara composition include those described above with reference to the primer composition. According to certain embodiments of the invention the colorant may be an inorganic particulate such as carbon black, ultramarines, or iron oxide. The concentration of colorant may range from about 2.5% to 10% by weight, such as from about 4% to about 8% colorant.

Suitable waxes for use in the mascara composition include those described above with reference to the primer composition. In certain embodiments of the invention the waxes are selected from beeswax, paraffin wax, glyceryl behenate, glyceryl dibehenate, tribehenin, hydrogenated oils such as hydrogenated jojoba or palm oil. The concentration of wax may range from about 10% to 25% by weight.

Suitable polymers for use in the mascara composition include film-forming polymers including those described above with reference to the primer composition. In certain embodiments of the invention the film-forming polymers are selected from polyacrylates, acrylates copolymers, quaternized polymers, and cellulose polymers. Other suitable polymers include hydrolyzed or unhydrolyzed natural starches/gums and particulate polymers such as polyethylene, PMMA, nylon and the like. The concentration of polymers may range from about 3% to 10% by weight.

According to certain embodiments, the mascara composition includes a polymer suitable for thickening the water phase. Suitable polymers include any of various natural thickening polymers including polysaccharides such as vegetable starches, pectins or vegetable gums (e.g., alginin, guar gum, locust bean gum, xanthan gum), or modified cellulose polymers (e.g., hydroalkyl cellulose polymers), proteins, or polyacrylate derivatives. The concentration of the thickening polymer may be from about 0.5% to about 10%, such as from about 1.0% to about 8%, such as from about 1.5% to about 6%.

Suitable emulsifiers for use in the mascara composition include anionic, amphoteric, and non-ionic emulsifiers suitable for emulsifying fatty compounds in a water phase. In certain embodiments of the invention, the emulsifiers are selected from fatty acids, fatty acid esters of glycerol and/or polyalkylene glycols, amphoacetates, and alkyl phosphates. In certain embodiments of the invention, the emulsifiers are selected from stearic acid, glyceryl stearate, peg-200 glyceryl stearate, steareth-2, steareth-20 isoceteth-20, and potassium cetyl phosphate, and disodium cocoamphoacetate. The concentration of emulsifiers may range from about 5% to 25% by weight such as from about 5% to about 10%.

The mascara compositions may include any of various additional ingredients such as one or more of fillers such as silica; 2% to 6% glycols such as glycerin, propylene glycol; 0.1% to about 12% of silicone oils such as dimethicone, simethicone, and cyclopentasiloxane; 0-4% C2-C3 monoalcohols; 0-3% C2-C3 alcohol, and 0% to about 10% preservatives, vitamins, extracts, active ingredients and the like.

Methods

Primer compositions used in the present invention may be made by mixing at least one non-ionic, water-soluble or water-dispersible copolymer including a cyclic amide monomer, a cyclic amine monomer, and an acrylamide monomer in water until dissolution. This polymer and other water-soluble ingredients may be mixed by stirring, shaking, grounding, or beating, optionally with a stirrer, a magnetic stirrer, a shaker, a homogenizer, or any other methods suitably used to mix cosmetic composition. The mixing may be carried out with or without heating or cooling the ingredients. Particulates and other ingredients that are to be dispersed are then added with mixing to form a homogeneous mixture.

Mascara compositions used in the present invention may be made by various means known to the art of mascara manufacture, and in particular emulsion mascaras, such as by preparing a water phase by charging a vessel with water, applying heat and adding colorants, any water-soluble emulsifiers, water soluble or dispersible polymers, optional preservatives and the like, and mixing. A fatty phase can be separately prepared by charging a vessel with waxes and other oil-soluble ingredients (e.g. hydrocarbon oils and silicone oils), heating, then adding the oil phase to the water phase and mixing/homogenizing for a time period sufficient to create a homogeneous mascara product.

One skilled in the art will recognize that critical shear rate of the mascara composition can be adjusted upward by, for example, decreasing the concentration of the water phase relative to the oil phase, increasing the concentration of water-phase thickener, increasing the concentration of pigments and/or fillers, or reducing the concentration of water. Similarly, critical shear rate can be adjusted downward by, for example, increasing the concentration of the water phase relative to the oil phase, decreasing the concentration of water-phase thickener, decreasing the concentration of pigments and/or fillers, increasing the concentration of water or increasing a concentration of C2-C3 alcohol.

One embodiment of the present invention provides a method of improving curl of keratinous materials. The primer composition described above is applied onto the keratinous materials. The keratinous materials are preferably keratin fibers, in particular eyelashes and eyebrows, but especially eyelashes. The primer composition is applied onto the keratinous materials in an amount sufficient to improve the curl of the keratinous materials and/or to permit a subsequently applied mascara composition to do so. To improve the curl of keratin fibers, the primer composition may be applied onto the keratin fibers in an amount sufficient to increase the curl, and also a volume and/or length of the keratin fibers. The primer is applied to a portion of keratinous surface that one desires to adopt a concave curvature, such as the top surface of the upper eyelash and allowed to dry. Accordingly, the primer compositions may be brushed or applied onto the eyelashes with attentiveness to apply it predominantly on the top surface of the top eyelashes rather than the bottom surface of the top eyelashes. The primer composition may be allowed to dry, such as for one to ten minutes. The mascara composition is then applied over the (dried) primer composition.

The way by which the primer and mascara compositions are applied onto the keratinous materials is not limited. Preferably, the mascara composition is applied onto keratin fibers by a brush, a wand, or a comb.

The compositions may be applied to eyelashes as needed, preferably once or twice daily, more preferably once daily and then preferably allowed to dry before subjecting to contact such as with clothing or other objects.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective measurements.

Examples

Strain sweeps were conducted for each of various commercial mascara compositions using a Discovery HR-3 Rheometer available from TA Instruments of New Castle, Del. and data was collected for complex modulus, G* versus strain to an oscillation strain of 1000%. This was conducted at a fixed angular frequency of 1 rad/s. The complex modulus G* is defined as below:

$$G^* = \sqrt{G'^2 + G''^2}$$

where G' and G" are storage and loss moduli, respectively. The complex modulus measured at 1% strain, "$G^*_{1\%}$," was recorded in Table 1. Furthermore, the flows were also conducted by measuring viscosity as a function of shear rate from 0.01 (1/s) to 1000 (1/s). The viscosity measured at shear rate of 0.1 (1/s) "$\eta_{0.1}$," was also recorded in Table 1.

Furthermore, an approximation for the slope of the high shear rate region of the viscosity versus shear rate curve was recorded as "shear thinning slope."

The various mascara compositions, each in combination with the above primer composition, were tested for SELF-CURLING using the following SELF-CURLING TEST. Using a flat iron, hair fiber strands (fake eyelashes), 12 mm in length secured between metal plates—available from SP Equation of Pourcieux, France—were straightened by gently stroking them using a commercially available hair straightener set to 450° F. for a sufficient period to straighten the fibers. Using a tongue depressor, a primer composition was applied to the fake eyelashes, stroked ten times on one side of the simulated eyelashes and immediately followed by mascara. The primer composition is consistent with embodiments of the invention and was prepared by dissolving LUVISET CLEAR AT3 into a formula that included a fixed amount of SIMULGEL 600 (Seppic, Inc of Fairfield, N.J.), PROTANAL PH 6160, carbon black and water (q.s.). The primer composition deposits approximately 2 mg to 10 mg of composition. Various commercially available mascara compositions to be tested were then applied to the fake eyelashes and stroked ten times on one side of the simulated eyelashes. The treated lashes were put into a humidity chamber (25% RH and 32° C.) for 5 minutes. A curl measurement was then taken by placing a protractor near the eyelashes and visually estimating the angle of curl relative to the horizontal surface of the metal plate within which the fake eyelashes are secured. The result ("Initial Curl") was recorded as either "Poor" (no visible curling) or "Good" (significant visible curling). If the degree of curl of the fake eyelashes was less than 15 degrees, the result was recorded as Poor, otherwise it was recorded as "Good." The curl measurements are recorded in Table 2.

Also shown in Table 2 is a calculated parameter, the "critical shear rate," which, as one skilled in the art will readily recognize, is determined from the inflection point (of the 'plateau') in the viscosity versus shear rate curve. An example is shown in The FIGURE, where line 100 identifies the critical shear rate.

The results for $G^*_{1\%}$, $\eta_{0.1\%}$, and shear thinning slope are shown in Table 1. The results of the critical shear rate for the mascara compositions as well as the SELF-CURLING TEST performed after applying the mascara composition over the primer composition are shown in Table 2 below.

TABLE 1

Initial Curl and Critical Shear Rate

| Example | Mascara Composition | Complex Shear Modulus, $G^*_{1\%}$ (Pa) | Viscosity, $\eta_{0.1}$ (Pa · s) | Shear Thinning Slope (Pa · s$^2$) |
|---|---|---|---|---|
| Comparative Example 1 | Colossal (Maybelline) | 3706.13 | 364.4 | −0.6 |
| Inventive Example 1 | Million Lashes (L'Oreal Paris) | 3630 | 751.6 | −0.71 |
| Inventive Example 2 | Hypnose Doll Eyes (Lancome) | 4879 | 732 | −0.65 |
| Inventive Example 3 | Falsies (Maybelline) | Not tested | 522 | −0.75 |
| Inventive Example 4 | Definicils (Lancome) | 4099 | 259.81 | −0.74 |
| Inventive Example 5 | Temptation (Maybelline) | 3206 | 680 | −0.89 |
| Inventive Example 6 | Lash Paradise (L'Oreal Paris) | 7521.6 | 973.7 | −0.901 |
| Inventive Example 7 | Feline (L'Oreal Paris) | 6648 | 919.8 | −0.93 |
| Inventive Example 8 | Voluminous Original (L'Oreal Paris) | 5203 | 571.8 | −0.83 |
| Inventive Example 9 | Full N Soft (Maybelline) | Not tested | 223.4 | −0.69 |
| Comparative Example 2 | Christian Dior OverCurl (Dior) | 9820.2 | 1629 | −0.77 |
| Comparative Example 3 | Better Than Sex (Too Faced Cosmetics) | 8972 | 2012.7 | −0.81 |

TABLE 2

Initial Curl and Critical Shear Rate

| Example | Mascara Composition | Initial Curl | Critical Shear Rate (1/s) |
|---|---|---|---|
| Comparative Example 1 | Colossal (Maybelline) | Poor | 2.37 |
| Inventive Example 1 | Million Lashes (L'Oreal Paris) | Good | 5.04 |
| Inventive Example 2 | Hypnose Doll Eyes (Lancome) | Good | 2.5 |
| Inventive Example 3 | Falsies (Maybelline) | Good | 20.23 |
| Inventive Example 4 | Definicils (Lancome) | Good | 21.35 |
| Inventive Example 5 | Temptation (Maybelline) | Good | 14.8 |
| Inventive Example 6 | Lash Paradise (L'Oreal Paris) | Good | 38.97 |
| Inventive Example 7 | Feline (L'Oreal Paris) | Good | 45.61 |
| Inventive Example 8 | Voluminous Original (L'Oreal Paris) | Good | 15.3 |
| Inventive Example 9 | Full N Soft (Maybelline) | Good | 10.2 |
| Comparative Example 2 | Christian Dior OverCurl (Dior) | Poor | 103.7 |
| Comparative Example 3 | Better Than Sex (Too Faced Cosmetics) | Poor | 244.4 |

The inventive compositions included about 40%-55% water; about 4% to 8% colorant (pigment); about 10% to 25% wax; and about 5% to 10% emulsifier and were in the form of oil-in water emulsions. The results indicate that mascara compositions that include water; colorant; wax; and emulsifier and have a critical shear rate from 2.5/s to 100/s when used over a primer composition including a water dispersible copolymer comprising a cyclic amide monomer, a cyclic amine monomer, and an acrylamide monomer have surprisingly good curl performance. Those mascara compositions that fall outside the above critical shear rate do not have good curl performance.

What is claimed is:

1. A kit, comprising:
  a primer composition, comprising:
    water; and
    a non-ionic and water-soluble or water dispersible copolymer comprising a cyclic amide monomer, a cyclic amine monomer, and an acrylamide monomer, wherein the primer composition does not contain a quaternized polymer; and a mascara composition, comprising:
  water;
  colorant;
  wax;
  emulsifier; and
  one or more second polymers different than the non-ionic and water-soluble or water dispersible copolymer in the primer composition; wherein the mascara composition has a critical shear rate from 2.5/s to 100/s.

2. The kit of claim 1 wherein the non-ionic and water-soluble or water dispersible copolymer is present in a concentration by weight in the primer composition that is from about 10 percent to about 60 percent.

3. The kit of claim 1, wherein the non-ionic and water-soluble or water dispersible copolymer is present in a concentration by weight in the primer composition that is from about 15 percent to about 60 percent.

4. The kit of claim 1 wherein the non-ionic and water-soluble or water dispersible copolymer is a copolymer of N-vinyl pyrrolidone, methacrylamide, and N-vinylimidazole.

5. The kit of claim 1, wherein the primer composition is substantially free of wax.

6. The kit of claim 1, wherein the primer composition is substantially free of colorant.

7. The kit of claim 1, wherein the primer composition comprises from 15% to 60% of the non-ionic and water-soluble or water dispersible copolymer, wherein the non-ionic and water-soluble or water dispersible copolymer is a copolymer of N-vinyl pyrrolidone, methacrylamide, and N-vinylimidazole, wherein the primer composition is substantially free of wax and wherein the primer composition is substantially free of colorant.

8. The kit of claim 1, wherein the mascara composition comprises 25% to 65% by weight of water;
  2.5% to 10% by weight of colorant;
  10% to 25% by weight of wax;
  3% to 10% of one or more second polymers different than the non-ionic and water-soluble or water dispersible copolymer in the primer composition; and
  5% to 10% by weight of emulsifier.

9. The kit of claim 1, wherein the mascara composition has a critical shear rate from 2.5/s to 50/s.

10. A method of making up eyelashes, comprising:
  applying the primer composition of claim 1 to said eyelashes; and
  applying to said eyelashes having the primer composition previously applied thereto, the mascara composition of claim 1.

11. The method of claim 10, wherein the non-ionic and water-soluble or water dispersible copolymer is present in a concentration by weight in the primer composition that is from about 10 percent to about 60 percent.

12. The method of claim 10, wherein the non-ionic and water-soluble or water dispersible copolymer is present in a concentration by weight in the primer composition that is from about 15 percent to about 60 percent.

13. The method of claim 10, wherein the non-ionic and water-soluble or water dispersible copolymer is a copolymer of N-vinyl pyrrolidone, methacrylamide, and N-vinylimidazole.

14. The method of claim 10, wherein the primer composition is substantially free of wax.

15. The method of claim 10, wherein the primer composition is substantially free of colorant.

16. The method of claim 10, wherein the primer composition comprises from 15% to 60% of the non-ionic and water-soluble or water dispersible copolymer, wherein the non-ionic and water-soluble or water dispersible copolymer is a copolymer of N-vinyl pyrrolidone, methacrylamide, and N-vinylimidazole, wherein the primer composition is substantially free of wax and substantially free of colorant.

17. The method of claim 10, wherein the mascara composition comprises
  25% to 65% by weight of water;
  2.5% to 10% by weight of colorant;
  10% to 25% by weight of wax;
  3% to 10% of one or more second polymers; and
  5% to 10% by weight of emulsifier.

18. The method of claim 10, wherein the mascara composition has a critical shear rate from 2.5/s to 50/s.

* * * * *